(12) United States Patent
Liu et al.

(10) Patent No.: US 10,959,963 B2
(45) Date of Patent: Mar. 30, 2021

(54) METHOD FOR THE TREATMENT OF FATTY LIVER DISEASE

(71) Applicant: Golden Biotechnology Corporation, Jersey City, NJ (US)

(72) Inventors: Sheng-Yung Liu, New Taipei (TW); Wu-Che Wen, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 16/699,405

(22) Filed: Nov. 29, 2019

(65) Prior Publication Data

US 2020/0093757 A1    Mar. 26, 2020

Related U.S. Application Data

(63) Continuation of application No. 15/633,719, filed on Jun. 26, 2017, now abandoned, and a continuation of application No. 13/801,697, filed on Mar. 13, 2013, now abandoned.

(51) Int. Cl.
| | | |
|---|---|---|
| *A61K 31/56* | (2006.01) |
| *A61K 31/122* | (2006.01) |
| *A61K 31/575* | (2006.01) |
| *A61K 9/48* | (2006.01) |
| *A61K 9/00* | (2006.01) |
| *A61K 36/07* | (2006.01) |

(52) U.S. Cl.
CPC .......... *A61K 31/122* (2013.01); *A61K 9/0056* (2013.01); *A61K 9/0078* (2013.01); *A61K 9/4875* (2013.01); *A61K 31/575* (2013.01); *A61K 36/07* (2013.01)

(58) Field of Classification Search
CPC ........................... A61K 31/122; A61K 31/575
See application file for complete search history.

*Primary Examiner* — Shobha Kantamneni
(74) *Attorney, Agent, or Firm* — Chang-Hsing Liang

(57) ABSTRACT

The invention provides a method of treating, inhibiting and/or preventing fatty liver disease in a patient in need thereof, comprising administering an effective amount of a cyclohexenone compound of the following formula (I) to said patient,

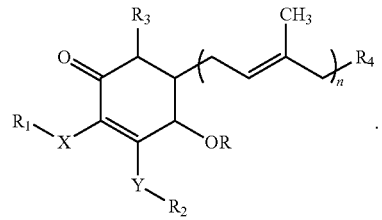

2 Claims, 17 Drawing Sheets

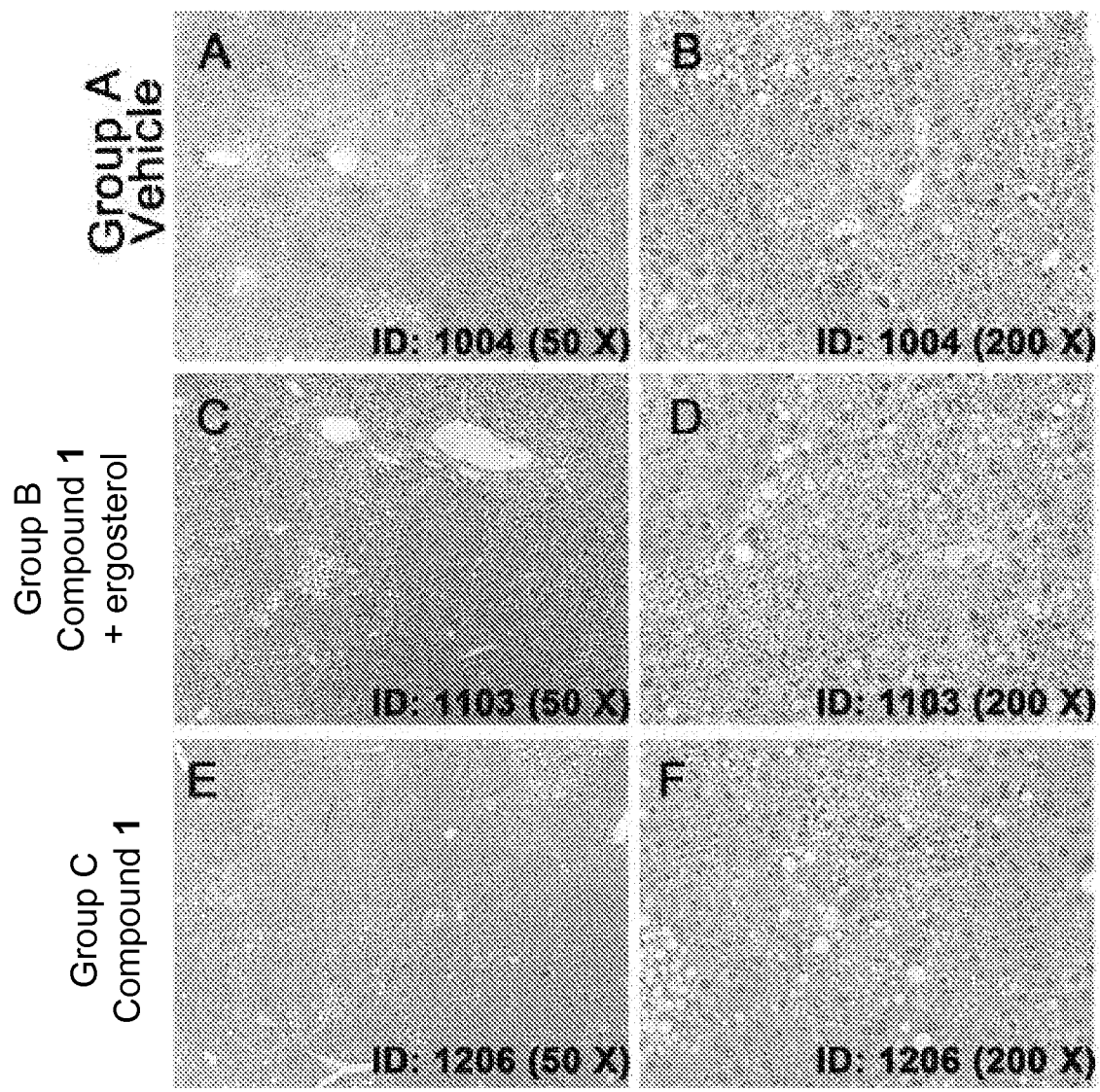
FIG. 15 (A-F)

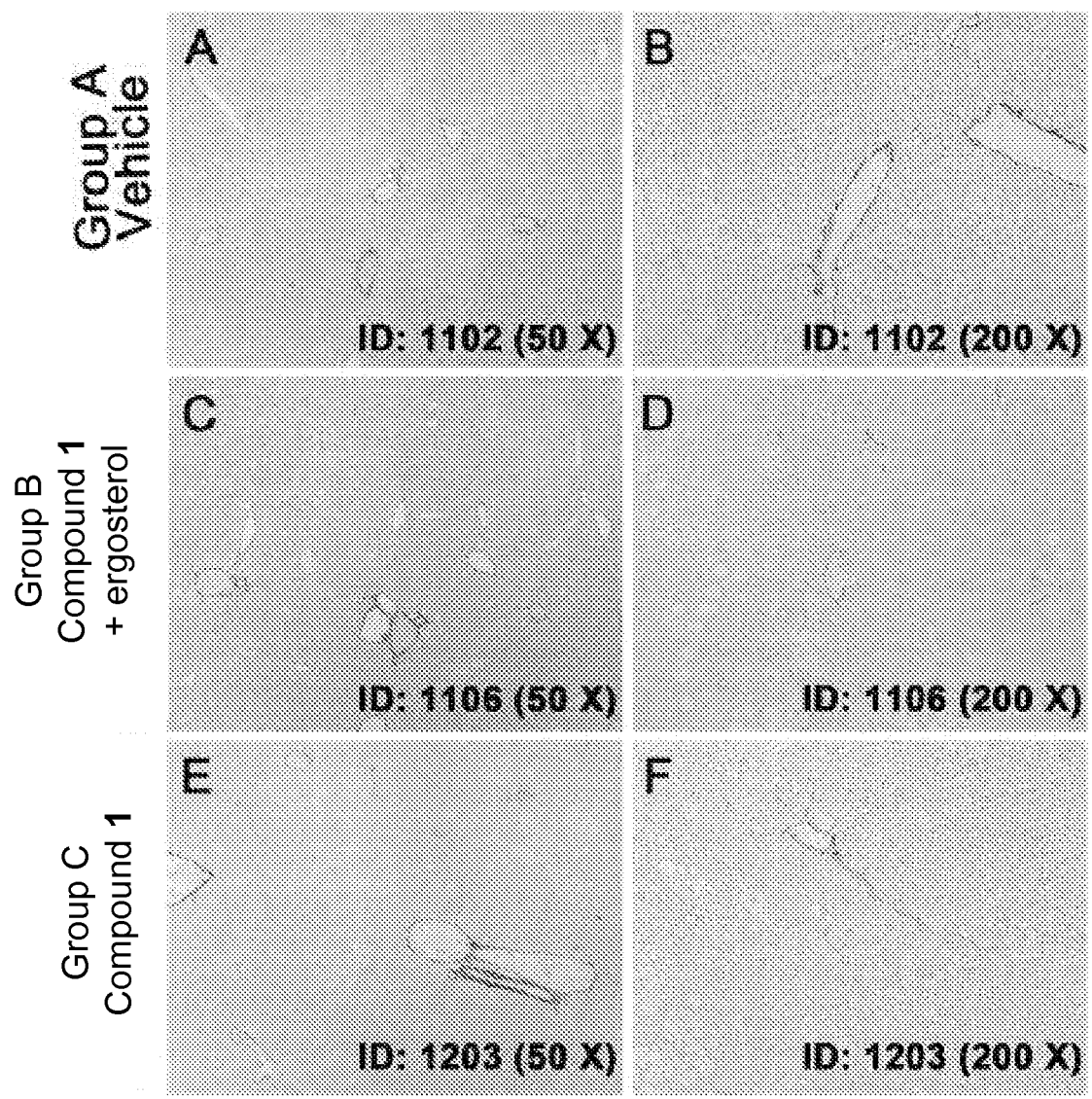
FIG. 16 (A-F)

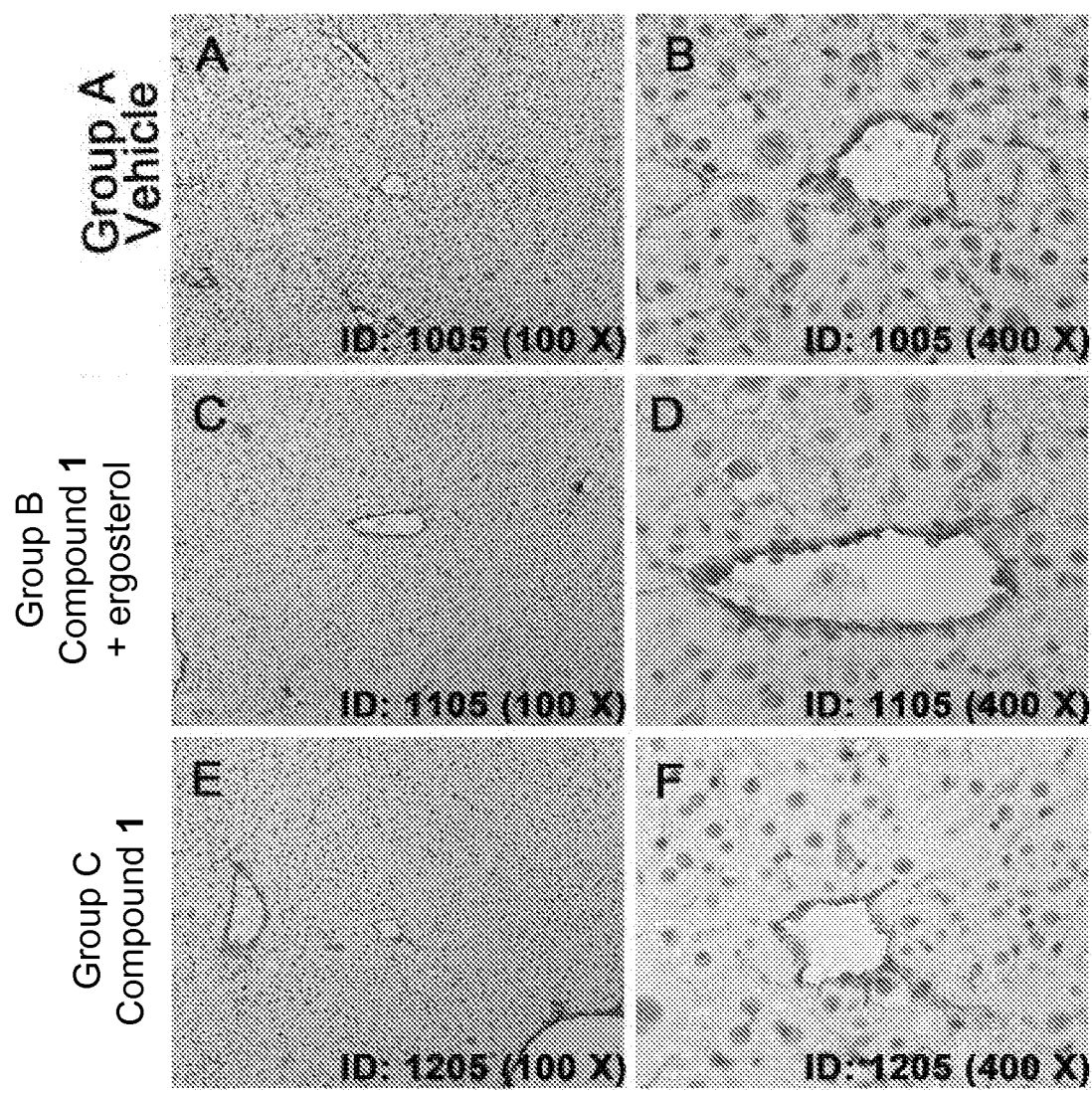
FIG. 17 (A-F)

METHOD FOR THE TREATMENT OF FATTY LIVER DISEASE

FIELD OF THE INVENTION

The present invention relates to a method for the treatment of fatty liver disease, and more particularly, to a method of administering a cyclohexenone compound.

BACKGROUND OF THE INVENTION

Fatty liver refers to a pathogenic condition where fat comprises more than 5% of the total weight of the liver. Fatty liver and steatohepatitis are frequently found in people who intake excessive alcohols and who have obesity, diabetes, hyperlipidemia, etc. Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). In NASH, the fat accumulation is associated with varying degrees of inflammation (hepatitis) and scarring (fibrosis) of the liver. The NAFLD spectrum is thought to begin with and progress from its simplest stage, called simple fatty liver (steatosis). That is, fatty liver is the initial abnormality in the spectrum of NAFLD. Simple fatty liver involves just the accumulation of fat in the liver cells with no inflammation or scarring. The fat is actually composed of a particular type of fat (triglyceride) that accumulates within the liver cells. Fatty liver is a harmless (benign) condition. The next stage and degree of severity in the NAFLD spectrum is NASH. As mentioned, NASH involves the accumulation of fat in the liver cells as well as inflammation of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. Strong evidence suggests that NASH, in contrast to simple fatty liver, is not a harmless condition. This means that NASH can ultimately lead to scarring of the liver (fibrosis) and then irreversible, advanced scarring (cirrhosis). Cirrhosis that is caused by NASH is the last and most severe stage in the NAFLD spectrum.

There are few therapeutically effective drugs for treating fatty liver. Exercise and controlled diet are recommended, but these are not so effective in treating fatty liver. Accordingly, development of a fatty liver treatment having superior effect and safety with no adverse reactions is in need.

SUMMARY OF THE INVENTION

The invention provides a method of treating, inhibiting and/or preventing fatty liver disease in a patient in need thereof, comprising administering an effective amount of a cyclohexenone compound of the formula (I) as described herein to said patient. In an exemplary embodiment, the cyclohexenone compound is administered with a second ingredient.

In one aspect provides methods of treating, inhibiting and/or preventing fatty liver disease in a patient in need thereof, comprising administering an effective amount of a cyclohexenone compound of the following formula (I) to said patient,

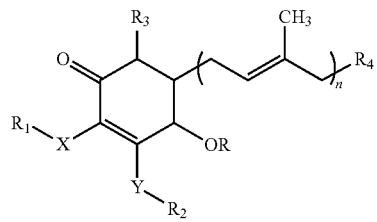

wherein each of X and Y independently is oxygen, $NR_5$ or sulfur;

R is a hydrogen or $C(=O)C_1\text{-}C_8\text{alkyl}$;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8\text{alkyl}$, $C_2\text{-}C_8\text{alkenyl}$, $C_2\text{-}C_8\text{alkynyl}$, aryl, glucosyl, wherein the 5 or 6-membered lactone, $C_1\text{-}C_8\text{alkyl}$, $C_2\text{-}C_8\text{alkenyl}$, $C_2\text{-}C_8\text{alkynyl}$, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8\text{alkyl}$;

$R_7$ is a $C_1\text{-}C_8\text{alkyl}$, $OR_5$ or $NR_5R_6$;

m=1-12; and n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

FIGS. 1(A) and 1(B) show HE-stained sections of livers of Group A at an enlargement ratio of 50× enlargement ratio of 200×, respectively. FIGS. 1(C) and 1(D) show HE-stained sections of livers of Group B at an enlargement ratio of 50× enlargement ratio of 200×.

FIGS. 2(A) and 2(B) show Sirius-red stained sections of livers of Group A at an enlargement ratio of 50× enlargement ratio of 200×, respectively. FIGS. 2(C) and 2(D) show Sirius-red stained sections of livers of Group B at an enlargement ratio of 50× enlargement ratio of 200×.

FIGS. 3(A) and 3(B) show collagen Type 3-immunostained sections of livers of Group A at an enlargement ratio of 50× enlargement ratio of 400×, respectively. FIGS. 3(C) and 3(D) show Sirius-red stained sections of livers of Group B at an enlargement ratio of 50× enlargement ratio of 400×.

FIGS. 8(A) and 8(B) show HE-stained sections of livers of Group A at an enlargement ratio of 50× enlargement ratio of 200×, respectively. FIGS. 8(C) and 8(D) show HE-stained sections of livers of Group B at an enlargement ratio of 50× enlargement ratio of 200×.

FIGS. 9(A) and 9(B) show Sirius-red stained sections of livers of Group A at an enlargement ratio of 50× enlargement ratio of 200×, respectively. FIGS. 9(C) and 9(D) show Sirius-red stained sections of livers of Group B at an enlargement ratio of 50× enlargement ratio of 200×.

FIGS. 10(A) and 10(B) show collagen Type 3-immunostained sections of livers of Group A at an enlargement ratio of 50× enlargement ratio of 400×, respectively. FIGS. 10(C) and 10(D) show Sirius-red stained sections of livers of Group B at an enlargement ratio of 50× enlargement ratio of 400×.

FIG. 15(A-F) shows representative photomicrographs of HE-stained sections of livers in a fatty liver condition assay in Group A (vehicle control), Group B (test compound & ergosterol) and Group C (test compound alone). FIGS. 15(A) and 15(B) show HE-stained sections of livers of Group A at an enlargement ratio of 50× enlargement ratio of 200×, respectively. FIGS. 15(C) and 15(D) show HE-stained sections of livers of Group B at an enlargement ratio of 50× enlargement ratio of 200×. FIGS. 15(E) and 15(F) show HE-stained sections of livers of Group C at an enlargement ratio of 50× enlargement ratio of 200×.

FIG. 16(A-F) shows representative photomicrographs of Sirius-red stained of livers from Group A to Group C. FIGS. 16(A) and 16(B) show Sirius-red stained sections of livers of Group A at an enlargement ratio of 50× enlargement ratio of 200×, respectively. FIGS. 16(C) and 16(D) show Sirius-red stained sections of livers of Group B at an enlargement ratio of 50× enlargement ratio of 200×. FIGS. 16(E) and 16(F) show Sirius-red stained sections of livers of Group C at an enlargement ratio of 50× enlargement ratio of 200×.

FIG. 17(A-F) shows representative photomicrographs of collagen Type 3-immunostained sections of livers from Group A to Group C. FIGS. 17(A) and 17(B) show collagen Type 3-immunostained sections of livers of Group A at an enlargement ratio of 50× enlargement ratio of 400×, respectively. FIGS. 17(C) and 17(D) show Sirius-red stained sections of livers of Group B at an enlargement ratio of 50× enlargement ratio of 400×. FIGS. 17(E) and 17(E) show Sirius-red stained sections of livers of Group C at an enlargement ratio of 50× enlargement ratio of 400×.

DETAILED DESCRIPTION OF THE INVENTION

Figure 1:
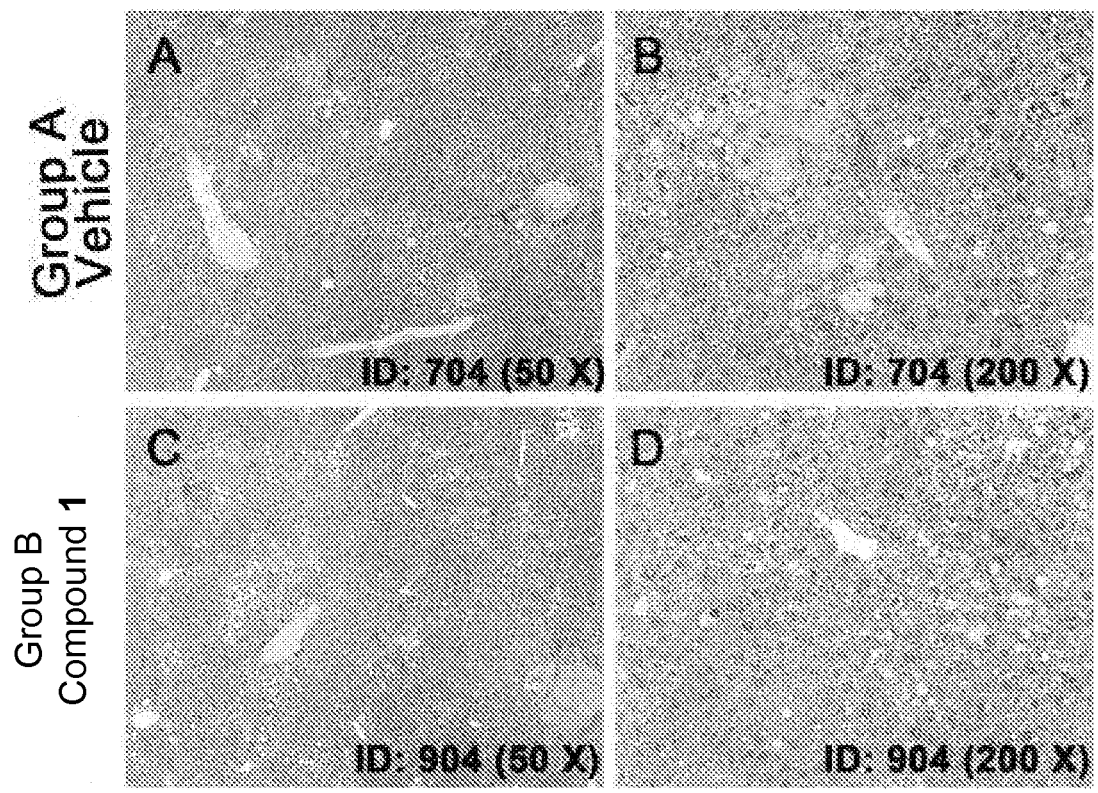
FIG. 1(A-D) shows representative photomicrographs of HE-stained sections of livers of Group A (vehicle control) and Group B (test compound, Compound 1) in a Fatty Liver Disease model.

In some embodiments, the invention surprisingly found that cyclohexenone compounds described herein effectively treat, inhibit and/or prevent fatty liver disease.

The terms "a" and "an" refer to one or to more than one (i.e., to at least one) of the grammatical object of the article.

The term "treat," "treatment" or "treating" means reducing the frequency, extent, severity and/or duration with which symptoms of fatty liver disease are experienced by a patient.

The term "prevent," "prevention" or "preventing" means inhibition, risk reduction, reducing the onset of or the averting of symptoms associated with fatty liver disease.

The term "pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

The term "effective amount" means an amount of the compound described herein effective to treat, inhibit and/or prevent fatty liver diseases. For example, the effective amount of the compound described herein reduces the number of fat cells; reduces the liver size; inhibits (i.e., slow to some extent and preferably stop) fatty cell infiltration; inhibits (i.e., slows at least to some extent and preferably stops) inflammation (hepatitis), scarring (cirrhosis) or necrosis; and/or relieves to some extent one or more of the symptoms associated with the disease.

Plants and mushrooms are a valuable resource for the discovery and development of novel, naturally derived agents to treat cancer. *Antrodia camphorata* is also called Chang-Zhi, Niu Chang-Gu, red camphor mushroom and the like, which is a perennial mushroom belonging to the order Aphyllophorales, the family Polyporaceae. It is an endemic species in Taiwan growing on the inner rotten heart wood wall of *Cinnamomum kanehirae* Hay. *C. kanehirai* Hay is rarely distributed and being overcut unlawfully, which makes *A. camphorata* growing inside the tree in the wild became even rare. The price of *A. camphorata* is very expensive due to the extremely slow growth rate of natural *A. camphorata* that only grows between Junes to October. Traditionally, *A. camphorata* is used as a Chinese remedy for food, alcohol, and drug intoxication, diarrhea, abdominal pain, hypertension, skin itches, and liver cancer. Triterpenoids are the most studied component among the numerous compositions of *A. camphorata*.

U.S. Pat. No. 7,385,088 is directed to a novel compound and use thereof, in particular to Antroquinonol B and Antroquinonol C isolated from *A. camphorata* extracts which effectively inhibit the growth of certain cancer cells. U.S. Pat. No. 7,342,137 provides cyclohexenone compounds and their uses in tumor growth inhibition, which is an extract isolated and purified from *A. camphorate*, in particular to 4-hydroxy-2,3-dimethoxy-6-methyl-5(3,7,11-trimethyl-dodeca-2,6,10-trienyl)-cyclohex-2-enone. Furthermore, several uses of the compound, 4-hydroxy-2,3-dimethoxy-6-methyl-5(3,7,11-trimethyl-dodeca-2,6,10-trienyl)-cyclohex-2-enone were developed. U.S. Pat. No. 7,411,003 discloses the use of 4-hydroxy-2,3-dimethoxy-6-methyl-5(3,7,11- trimethyl-dodeca-2,6,10-trienyl)-cyclohex-2-enone in inhibiting HBV. U.S. Pat. No. 7,456,225 discloses the use of 4-hydroxy-2,3-dimethoxy-6-methyl-5(3,7,11-trimethyl-dodeca-2,6,10-trienyl)-cyclohex-2-enone in liver protection such as alleviating liver injury and fibrosis induced by chemicals and reduces the serum levels of alanine aminotransferase (ALT) and aspartate aminotransferase (AST). U.S. Pat. No. 7,468,392 discloses the use of 4-hydroxy-2,3-dimethoxy-6-methyl-5(3,7,11-trimethyl-dodeca-2,6-10-trienyl)-cyclohex-2-enone in delaying fatigue. U.S. Pat. No. 7,501,454 relates to the use of 4-hydroxy-2,3-dimethoxy-6-methyl-5(3,7,11-trimethyl-dodeca-2,6,10-trienyl-)-cyclohex-2-enone in treating autoimmune diseases. U.S. Pat. No. 8,236,860 provides the use of 4-hydroxy-2,3-dimethoxy-6-methyl-5-(3,7,11-trimethyl-dodeca-2,6,10-trienyl)-cyclohex-2-enone in inhibiting the survival of pancreatic cancer cells. US 20110060055, US 20110060056, US 20110060057, US 20110060058 and US 20110060059 disclose the use of 4-hydroxy-2,3-dimethoxy-6-methyl-5(3,7,11-trimethyl-dodeca-2,6,10-trienyl-)-cyclohex-2-enone in inhibiting the survival of lymphoma, gastric cancer, skin cancer, ovarian cancer and bladder cancer cells, respectively.

However, none of prior references teaches and suggests that the above-mentioned cyclohexenone compound can be used in the treatment and/or prevention of fatty liver diseases, in particular NAFLD.

Accordingly, the invention provides a method of treating, inhibiting and/or preventing fatty liver diseases in a patient in need thereof, comprising administering an effective amount of a cyclohexenone compound of the following formula (I) to said patient,

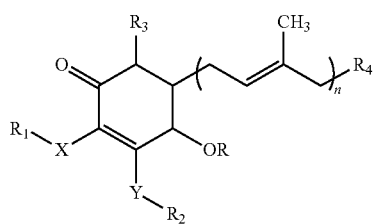

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$; $R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of $R_5$ and $R_6$ is independently a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

In some embodiments, the fatty liver diseases are the primary fatty liver diseases or the secondary fatty liver diseases. In some embodiments, the secondary fatty liver disease is alcohol liver disease, fatty liver associated with chronic hepatitis infection, total parental nutrition (TPN), Reye's Syndrome, gastrointestinal disorders, or gastroparesis and irritable bowel (IBS) disorders. In certain embodiments, the fatty liver disease is cirrhosis or fibrosis.

In some embodiments, the cyclohexenone compound having the following structure

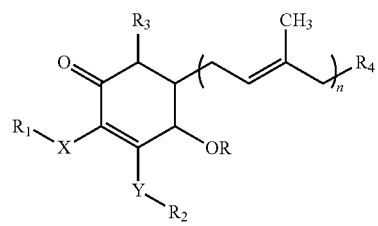

is prepared synthetically or semi-synthetically from any suitable starting material. In other embodiments, the cyclohexenone compound is prepared by fermentation, or the like. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

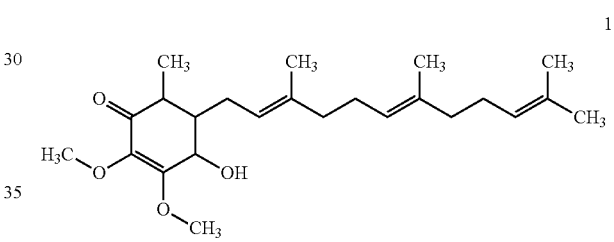

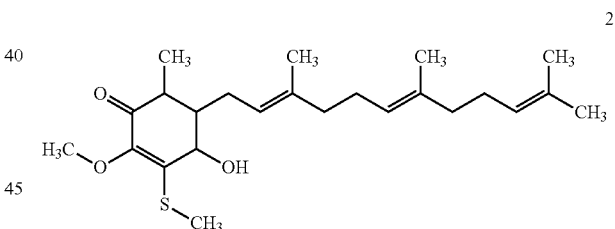

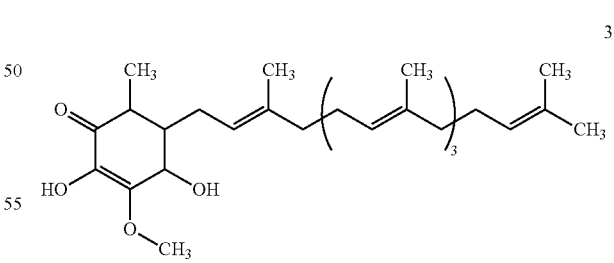

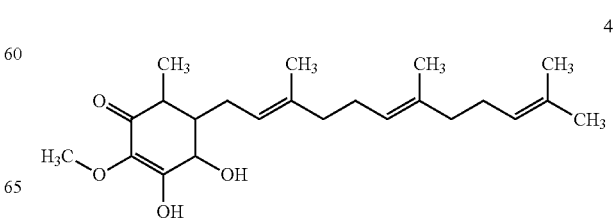

5
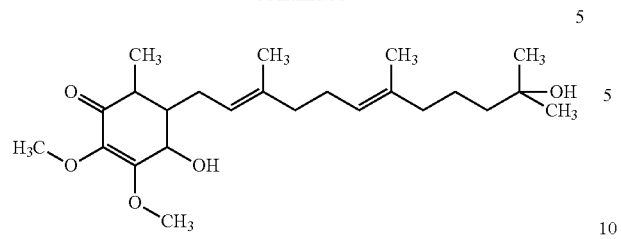
6
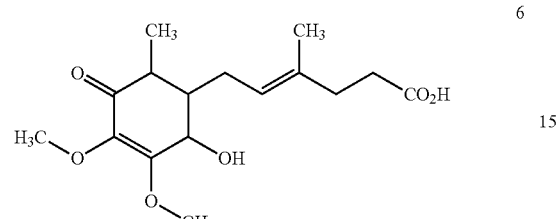
7
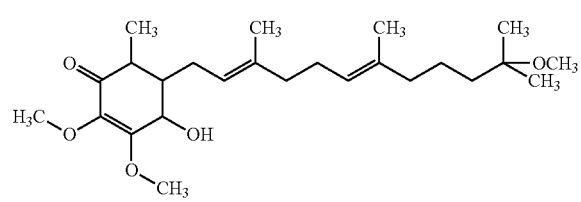
8
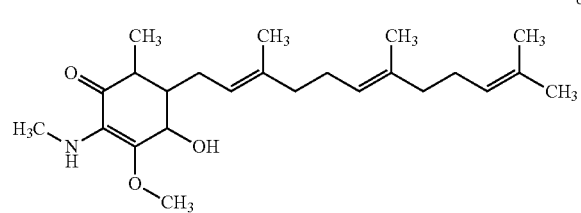
9
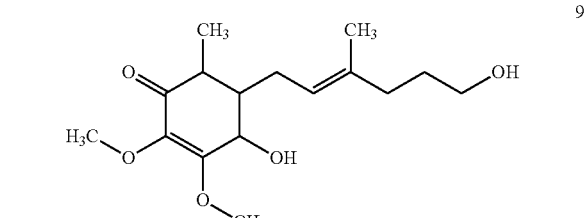
10
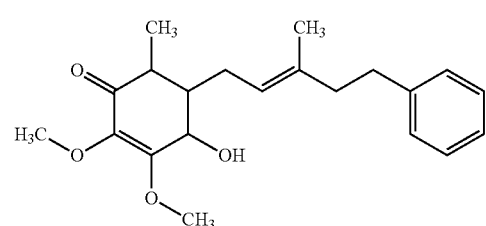
11
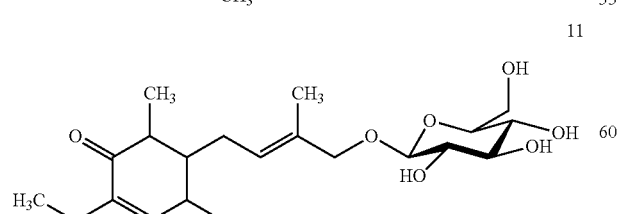
12
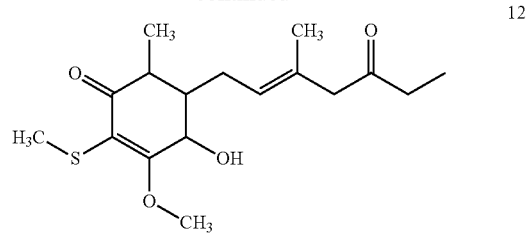
13
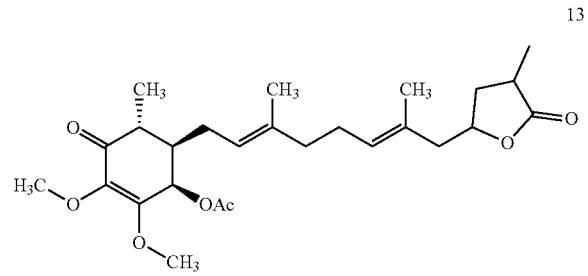
14
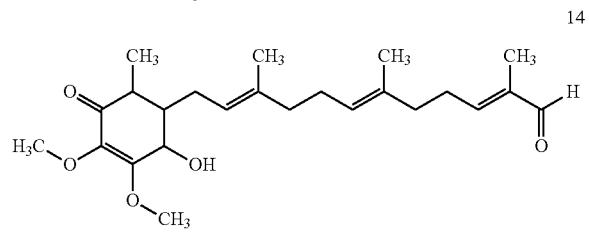
15
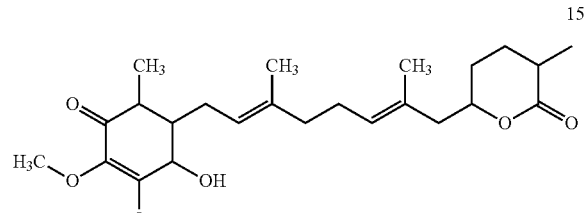
16
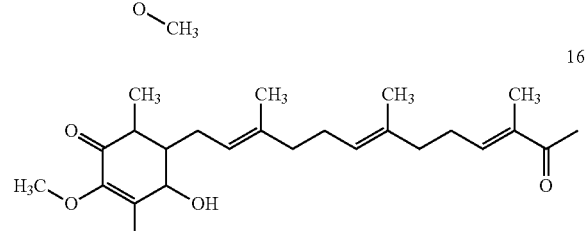
17
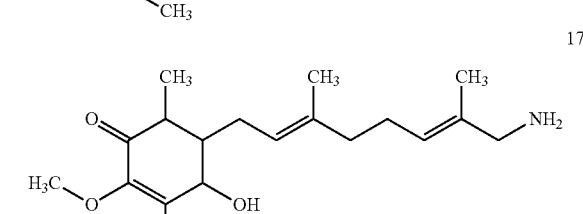
18
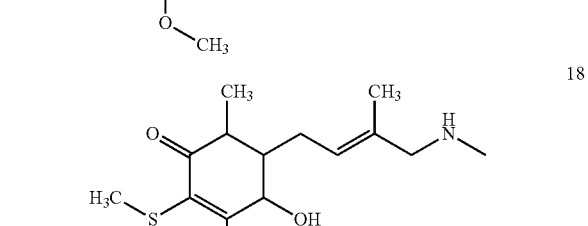

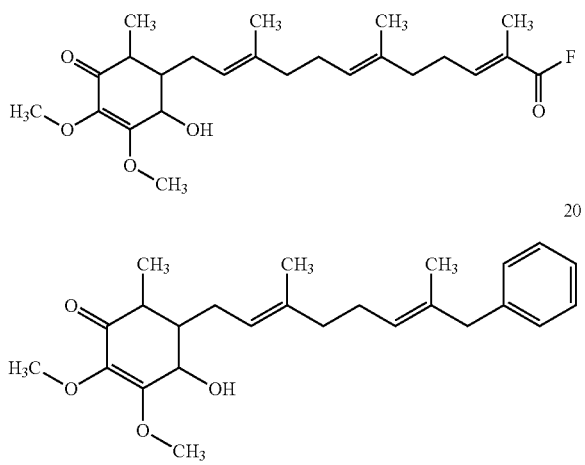

In other embodiments, the cyclohexenone compound having the structure

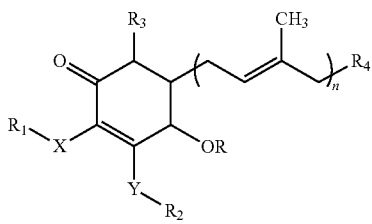

is isolated from the organic solvent extracts of *A. camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, or the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *A. camphorata*.

In some embodiments, R is a hydrogen, $C(=O)C_3H$, $C(=O)C_2H_5$, or $C(=O)CH_3$. In some embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, $C_1$-$C_8$alkyl, $C_2$-$C_8$alkenyl, $C_2$-$C_8$alkynyl, aryl, and glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

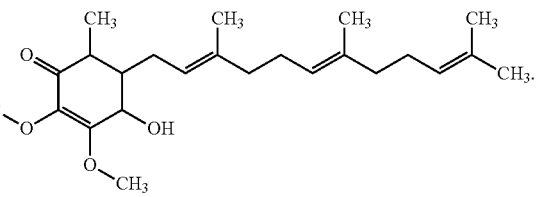

According to the invention, in some embodiments, the compounds provided herein are used in the treatment, inhibition and/or prevention of fatty liver disease. Examples of fatty liver diseases or liver disorders include the primary fatty liver diseases NAFLD and NASH and the secondary fatty liver diseases (e.g., alcoholic liver disease (ALD), fatty liver associated with chronic hepatitis infection, total parental nutrition (TPN), Reye's Syndrome, and gastrointestinal disorders such as Intestinal Bacterial Overgrowth (IBO), gastroparesis, irritable bowel (IBS) disorders, and the like). These examples are listed as examples only and the list is not intended to limit the treatment to these diseases.

Combination Treatments

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other fatty liver disease therapeutic agents are intended to be covered. In some embodiments, examples of fatty liver disease therapeutic agents include, but are not limited to, the following: ergosterol, vitamin E, selenium, betaine, insulin sensitizers (e.g., Metformin, Pioglitazone, Rosiglitazone, Thiazolidinediones, or the like), and statins, or the like.

The combinations of the cyclohexenone compounds and other fatty liver disease therapeutic agents described herein encompass additional therapies and treatment regimens with other agents in some embodiments. Such additional therapies and treatment regimens include another fatty liver disease therapy in some embodiments. Alternatively, in other embodiments, additional therapies and treatment regimens include other agents used to treat adjunct conditions associated with fatty liver disease or a side effect from such agent in the combination therapy. In further embodiments, adjuvants or enhancers are administered with a combination therapy described herein.

In some embodiment, the cyclohexenone compound of the invention is administered with a second ingredient. According to the invention, the second ingredient is ergosterol. The amounts of the cyclohexenone compound in combination with ergosterol range from 50% (w/w) to 90% (w/w) and 50% (w/w) to 10% (w/w), respectively. In general, the compositions described herein and, in embodiments where combinational therapy is employed based on the mode of action described herein, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, the compounds provided herein are administered by any convenient route, including oral, parenteral, subcutaneous, intravenous, intramuscular, intra peritoneal, or transdermal. The dosage administered depends upon the age, health, and weight of the recipient, kind of concurrent treatment, if any, and the nature of the effect desired.

In some embodiments, for administration, the compounds provided herein are mixed with one or more physiologically acceptable carriers comprising excipients and auxiliaries, which facilitate processing of the active compounds into preparations which are used pharmaceutically. Proper formulation is dependent upon the route of administration chosen.

In some embodiments, for oral administration, the compounds provided herein are formulated as discrete units such as capsules, cachets or tablets each containing a predetermined amount of the compound of the invention; as a powder or granules; as solution or a suspension in an aqueous liquid or a non-aqueous liquid; or as an oil-in-water liquid emulsion or a water-in-oil liquid emulsion.

In some embodiments, for injection, the compounds provided herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants, for example polyethylene glycol, are generally known in the art. In some embodiments, pharmaceutical compositions which are used orally, include push-fit capsules.

For administration by inhalation, the molecules for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit is determined by providing a valve to deliver a metered amount in some embodiments. Capsules and cartridges of, e.g., gelatin for use in an inhaler or insufflator, is formulated containing a powder mix of the polypeptide and a suitable powder base such as lactose or starch in some embodiments.

The dose will be determined by the activity of the compound produced and the condition of the subject, as well as the body weight or surface area of the subject to be treated. The size of the dose and the dosing regiment also will be determined by the existence, nature, and extent of any adverse side effects that accompany the administration of a particular compound in a particular subject. In determining the effective amount of the compound to be administered, the physician needs to evaluate circulating plasma levels, toxicity, and progression of the disease.

EXAMPLE

Example 1: Isolation of Exemplary Cyclohexenone Compounds 100 g of mycelia, fruiting bodies or mixture of both from *A. camphorata* were placed into a flask. A proper amount of water and alcohol (70-100% alcohol solution) was added into the flask and were stirred at 20-25 degrees Celsius (° C.) for at least 1 hour. The solution was filtered through a filter and a 0.45 μm (micrometer) membrane and the filtrate was collected as the extract. The filtrate of *A. camphorata* was subjected to a High Performance Liquid chromatography (HPLC). The HPLC was performed using a RP18 column, methanol (A) and 0.1~0.5% acetic acid (B) as the mobile phase, with gradient of 0~10 min in 95%-20% B, 10-20 min in 20%~10% B, 20~35 min in 10%~10% B, 35~40 min in 10%~95% B, at a flow rate of 1 ml/min. The effluent was monitored with a UV-visible detector.

The fractions at 25~30 min were collected and concentrated to yield Compound 1, 4-hydroxy-2,3-dimethoxy-6-methyl-5 (3,7,11-trimethyl-dodeca-2,6,10-trienyl)-cyclohex-2-enone, a product with the appearance of light yellow oil. The molecular formula, molecular weight and melting point of 4-hydroxy-2,3-dimethoxy-6-methyl-5 (3,7,11-trimethyl-dodeca-2,6,10-trienyl)-cyclohex-2-enone are $C_{24}H_{38}O_4$, 390, and 48° C. to 52° C., respectively. NMR spectra of the compound showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR (CDCl$_3$) δ (ppm)=1.21, 1.36, 1.67, 1.71, 1.75, 1.94, 2.03, 2.07, 2.22, 2.25, 3.68, 4.05, 5.71 and 5.56. $^{13}$C-NMR (CDCl$_3$) δ (ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

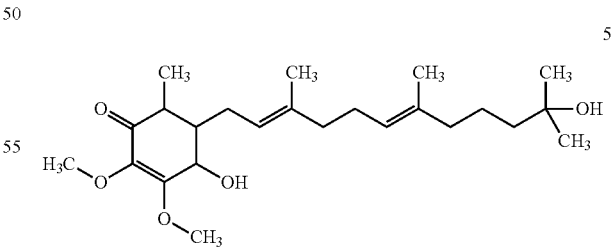

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy-2,3-dimethoxy-5-(11-methoxy-3,7,11-trimethyldodeca-2,6-dienyl)-6-methylcyclohex-2-enone with molecular weight of 422 ($C_{25}H_{42}O_5$). $^1$H-NMR ($CDCl_3$) δ (ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR ($CDCl_3$) δ (ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

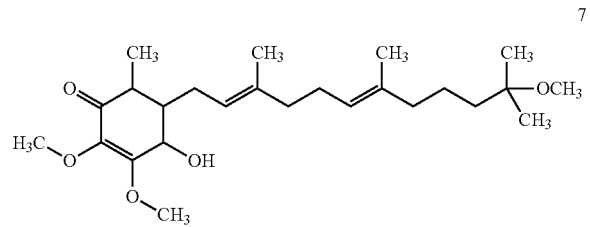

7

Compound 7: 4-hydroxy-2,3-dimethoxy-5-(11-methoxy-3,7,11-trimethyldodeca-2,6-dienyl)-6-methylcyclohex-2-enone Compound 6, a metabolite of Compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when Compound 1 was under the condition of above 40 OC for 6 hours.

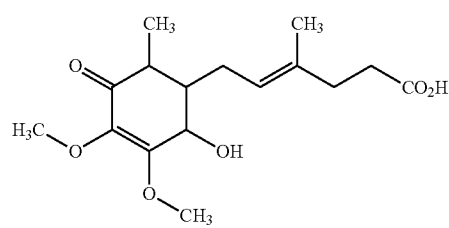

6

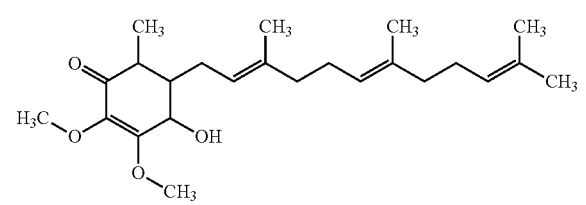 [SMILES: COC1=C(OC)C(O)C(C/C=C(\C)CC/C=C(\C)CCC=C(C)C)C(C)C1=O]

4

Alternatively, the exemplary compounds may be prepared from 4-hydroxy-2,3-dimethoxy-6-methylcyclohexa-2,5-dienone, or the like.

Similarly, other cyclohexenone compounds having the structure

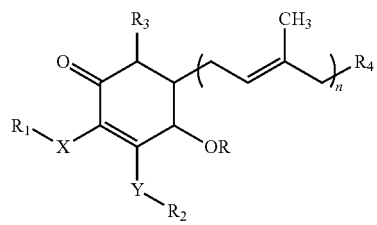

are isolated from *Antrodia camphorata* or prepared synthetically or semi-synthetically from the suitable starting materials. An ordinary person skilled in the art would readily utilize appropriate conditions for such synthesis.

Example 2: Reduction of Fatty Liver Condition by Compound 1 (4-hydroxy-2,3-dimethoxy-6-methyl-5 (3,7,11-trimethyl-dodeca-2,6-10-trienyl)-cyclohex-2-enone)

In order to simulate an unhealthy diet tendency in humans, such as excess consumption of high caloric food, the example constructs an animal model using rats fed a high fat diet to evaluate the effects of chronic liver injury. Thereafter, the effects can be revealed through biochemical assays to prove the fatty liver reduction of exemplary compounds provided herein such as Compound 1, 4-hydroxy-2,3-dimethoxy-6-methyl-5(3,7,11-trimethyl-dodeca-2,6-10-trienyl)-cyclohex-2-enone (the test compound).

The assay simulates liver disease caused by a high fat diet through a "Metabolic Syndrome" model. That is, the model is different from conventional chemical induced models caused by toxic components such as $CCl_4$. This model is distinguishable from the models caused by virus or alcohol.

The establishment of a long term high-fat diet is described as follows: First, the C57BL/6 mice were obtained from Charles River Laboratories Japan (Kanagawa, Japan). Animals were housed under specific-pathogen-free (SPF) conditions. The liver injury was developed in 18 male mice by subcutaneous injection of Streptozotocin (STZ) 2 days after birth (day 2). After 4 weeks, a high-fat commercial rodent diet ad libitum (CLEA JAPAN) were supplied. These mice were randomized into 3 groups before the treatment. The test compound was administered in a volume of 10 ml/kg twice a day for three weeks. In the control group (group A), six rats were fed with vehicle (corn oil from Sigma Chemical Co.) via intubation. Six mice in group B were orally administered vehicle and the test compound at a dose of 48 mg/kg twice a day (96 mg/kg per day). Table 1 summarizes the study timetable.

TABLE 1

| The timetable of the study | |
|---|---|
| Time | Process |
| Day 0 | Birth |
| Day 2 | STZ treatment |
| Day 28 | Feeding high fat diet |
| Day 62 | Randomization |
| Day 63-Day 76 | Test compound administration |
| Day 77 | Sacrifice |

Table 2 summarizes the treatment schedule.

TABLE 2

Experimental groups with the substances and dosages fed

| Group | No. mice | Test substance | Dosage (mg/kg) | Volume (ml/kg) | Regiments |
|---|---|---|---|---|---|
| A | 6 | Vehicle control | — | 10 | Oral, twice a day, 9-11 weeks |
| B | 6 | The test compound | 48 | | |

Histology Analysis (1) HE Staining. The HE staining method is performed as follows: Liver slices are cut from the livers' left side, embedded in Tissue-Tek® OCT™ Compounds (Sakura Finetek, Japan), snap frozen in liquid nitrogen, and stored at −80° C. 5 µm sections are cut, air-dried, fixed in acetone, air dried again and finally washed with phosphate buffered saline (PBS). Then, in the hematoxylin and eosin staining method, liver sections will be prefixed in a Bouin solution (formalin-acetic acid) for one week and then stained with Lillie-Mayer's Hematoxylin (Muto Pure Chemicals, Japan) and eosin solution (Wako, Japan) to visualize the lipid deposition, inflammations, cell necrosis and fibrosis, or stained with Masson's trichromic solution to visualize extra cellular matrix and collagen fibers of liver fibrosis development.

(2) Sirius Red Staining. The Sirius Red staining method is performed as follows: Liver slices are cut from the livers' left side, embedded in Tissue-Tek® OCT™ Compounds (Sakura Finetek, Japan), snap frozen in liquid nitrogen, and stored at −80° C. 5 µm sections are cut, air-dried, fixed in acetone, air dried again and finally washed with phosphate buffered saline (PBS). Then, liver sections are stained with a Picro-Sirius Red Solution (Waldeck GmbH & KG, Germany) to observe collagen deposition.

(3) Immunohistochemistry of Collagen Type 3. The immunohistochemistry assay for collagen Type 3 is performed as follows: Liver slices are cut from the livers' left side, embedded in Tissue-Tek® OCT™ Compounds (Sakura Finetek, Japan), snap frozen in liquid nitrogen, and stored at −80° C. 5 µm sections are cut, air-dried, fixed in acetone, air dried again and finally washed with phosphate buffered saline (PBS). For immunohistochemistry, endogenous peroxidase activity will be blocked by using 0.03% $H_2O_2$ for 5 minutes, followed by incubation with Block Ace (Dainippon Sumitomo Pharm, Japan) for 10 minutes. The sections will be incubated with the optimal dilution of anti-Type 3 collagen antibody overnight at 4° C. After incubation with an appropriate secondary antibody, the substrate reactions are performed using $DAB/H_2O_2$ solution (Nichirei, Japan).

Whole Blood and Plasma Biochemistry (1) Whole Blood Glucose. Blood samples were collected in heparinized syringes (Novo-Heparin 5,000 units/5 ml, Mochida Pharmaceutical, Japan) by cardiac puncture, kept on ice and centrifuged at 1,000×g at 4° C. for 15 minutes. The supernatant was collected and stored at −80° C. until use. Blood glucose was measured in whole blood samples using G Checker (Sanko Junyaku Co. Ltd., Japan).

(2) Plasma Aspartate aminotransferase (AST) and Alanine aminotransferase (ALT). The detection of plasma AST and ALT are performed as follows: Blood samples were collected in heparinized syringes (Novo-Heparin 5,000 units/5 ml, Mochida Pharmaceutical, Japan) by cardiac puncture and kept on ice then centrifuged at 1,000×g at 4° C. for 15 minutes. The supernatant was collected and stored at −80° C. until use. AST, ALT levels were measured by FUJI DRY CHEM 7000 (Fuji Film, Japan).

Fatty Liver Disease Caused by Non-Chemical Injury

FIG. 1 to FIG. 7 have proved that the exemplary compound extracted from *A. camphorata* (Compound 1) effectively decreases the extent of fatty liver disease caused by non-chemical injury. The decrease is assessed by evaluating the extent of liver injuries of fat deposition by histological analyses such as HE staining, Sirius red staining and collagen immunostaining, and further by plasma biochemical marker such as blood glucose, plasma triglyceride, plasma ALT and plasma AST.

HE staining reveals the morphology of hepatic cells under inflammatory cell infiltration, and macro- and micro-vesicular fat deposition. FIG. 1(A-D) shows the representative photomicrographs of HE-stained sections of livers of Group A and Group B, wherein FIGS. 1(A) and 1(C) show an enlargement ratio of 50× and FIGS. 1(B) and 1(D) show an enlargement ratio of 200×. As shown in FIGS. 1(A) and 1(B), the Group A (vehicle) diagrams revealed infiltration of inflammatory cells, macro- and micro vesicular fat deposition, proliferated bile ducts and hepato-cellular ballooning in the liver sections. As shown in FIGS. 1(C) and 1(D), group B (the test compound, Compound 1) treatment tended to decrease the infiltration of inflammatory cells and also tended to decrease the macro-vesicular fat deposition compared to Group A.

Figure 2:
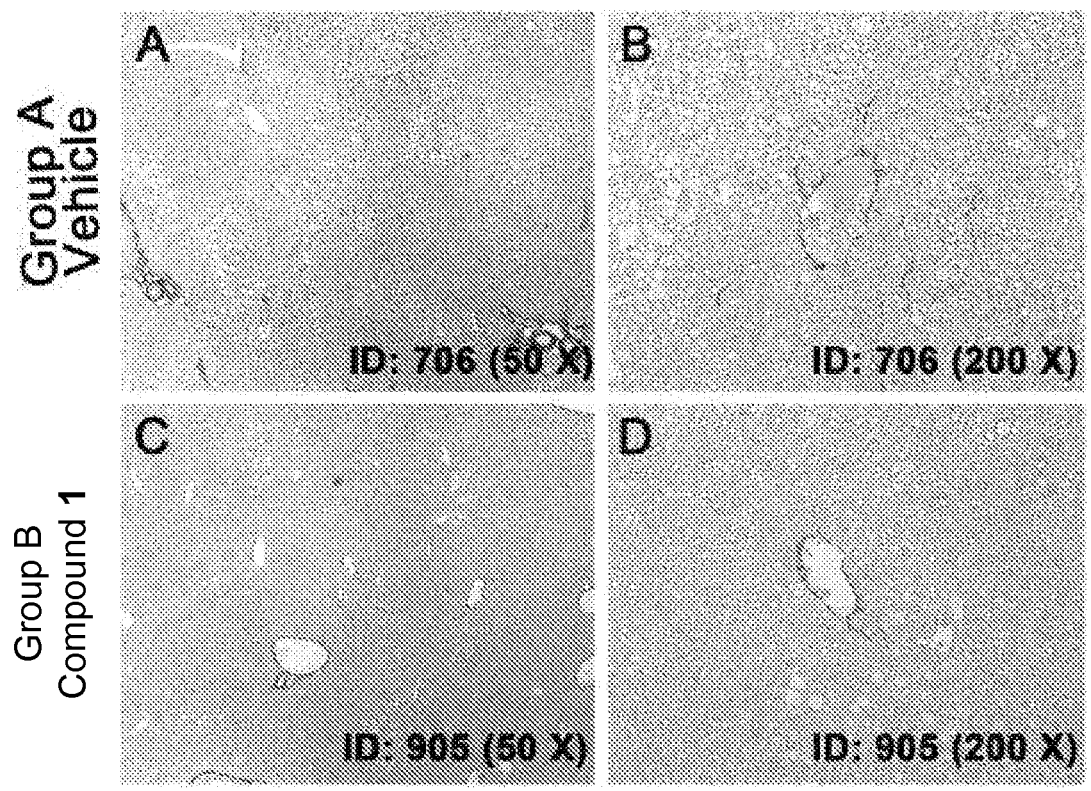
FIG. 2(A-D) shows representative photomicrographs of Sirius-red stained sections of livers of Group A and Group B Fatty Liver Disease model.

Sirius Red Staining is utilized to detect collagen deposition. FIG. 2 shows the representative photomicrographs of Sirius-red staining of livers of Group A and Group B, wherein FIGS. 2(A) and 2(C) show an enlargement ratio of 50× and FIGS. 2(B) and 2(D) show an enlargement ratio of 200×. As shown in FIGS. 2(A) and 2(B), in group A, Sirius red staining demonstrates collagen deposition around central veins, bile ducts and degenerative hepatocytes. As shown in FIGS. 2(C) and 2(D), in Group B (the test compound, Compound 1) treatment, the collagen deposition around the central veins and the bile ducts was reduced.

Figure 3:
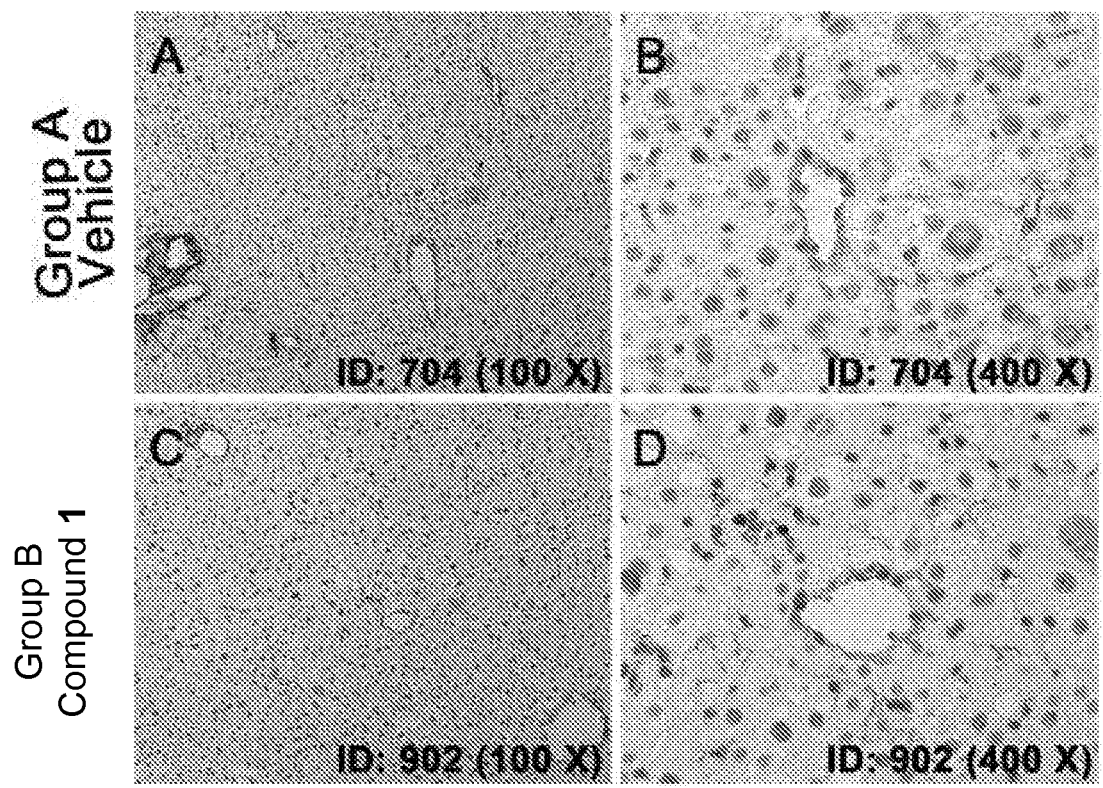
FIG. 3(A-D) shows representative photomicrographs of collagen Type 3-immunostained sections of livers of Group A and Group B Fatty Liver Disease model.

Collagen Type 3 staining is used to detect the distribution of collagen fibers. FIG. 3 shows the representative photomicrographs of collagen Type 3-immunostained sections of livers of Group A and Group B, wherein FIGS. 3(A) and 3(C) show an enlargement ratio of 50× and FIGS. 3(B) and 3(D) show an enlargement ratio of 400×. As shown in FIGS. 3(A) and 3(B), Collagen Type 3 staining shows accumulation of collagen fibers in the sinusoidal area and around bile ducts and central veins in the Vehicle control group A. As shown in FIGS. 3(C) and 3(D), the Group B (the test compound, Compound 1) treatment tended to reduce the thickness and/or the length of the collagen fibers in the sinusoidal area.

Figure 4:
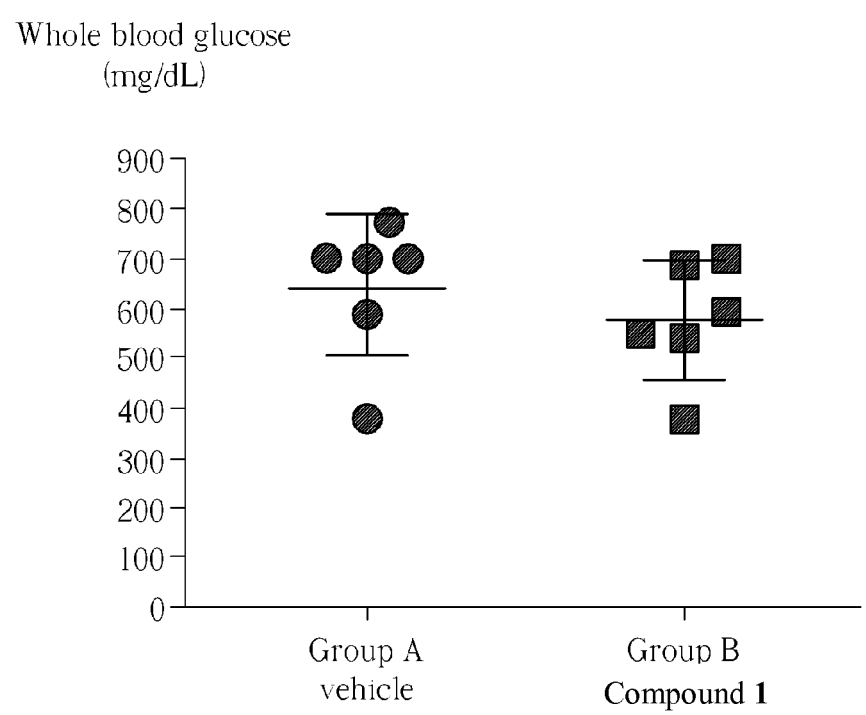
FIG. 4 shows diagrams of the whole blood glucose concentration (mg/dL) of Group A and Group B.

FIG. 4 shows the diagram of the whole blood glucose concentration (mg/dL) of Group A and Group B. As shown in FIG. 4, Group B treatment (the test compound, Compound 1) showed a decrease in the whole blood glucose level compared to the results of Group A treatment (Group A: 636±137 mg/dL, Group B: 580±122 mg/dL).

Figure 5:
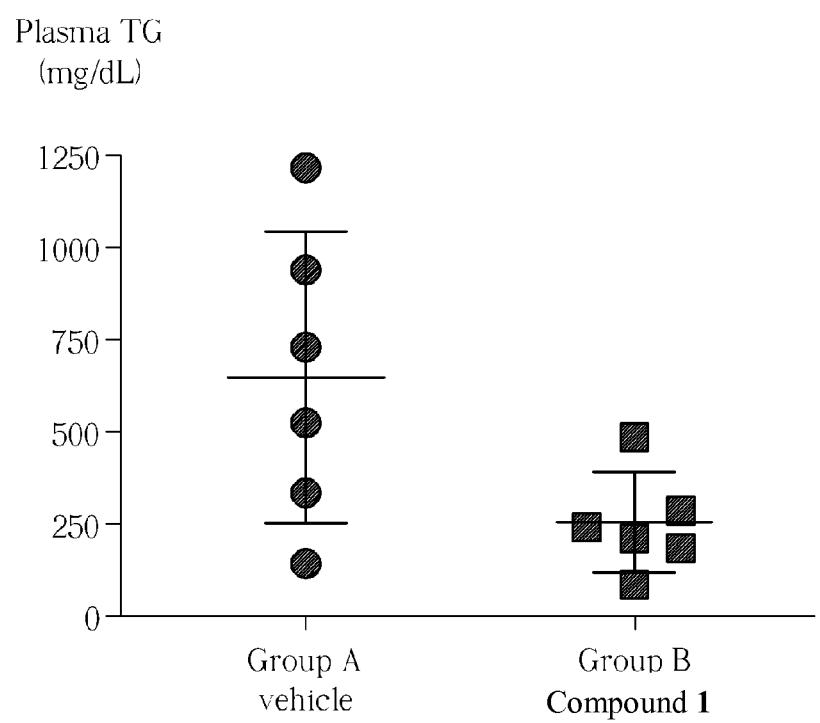
FIG. 5 shows diagrams of the plasma triglyceride concentration (mg/dL) of Group A and Group B.

FIG. 5 shows the diagram of the plasma triglyceride (TG) concentration (mg/dL) of Group A and Group B. As shown in FIG. 5, Group B treatment (the test compound, Compound 1) showed a significant decrease in the plasma TG compared to the results of Group A treatment (Group A: 643±402 mg/dL, Group B: 229±144 mg/dL).

Figure 6:
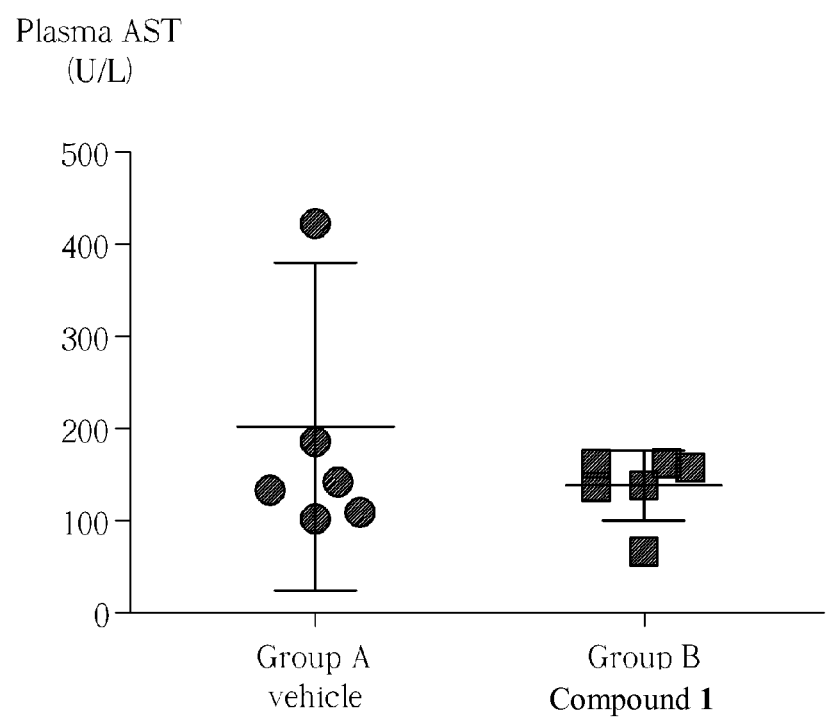
FIG. 6 and FIG. 7 respectively show diagrams of plasma AST and plasma ALT concentration (U/dL) of Group A and Group B.
Figure 7:
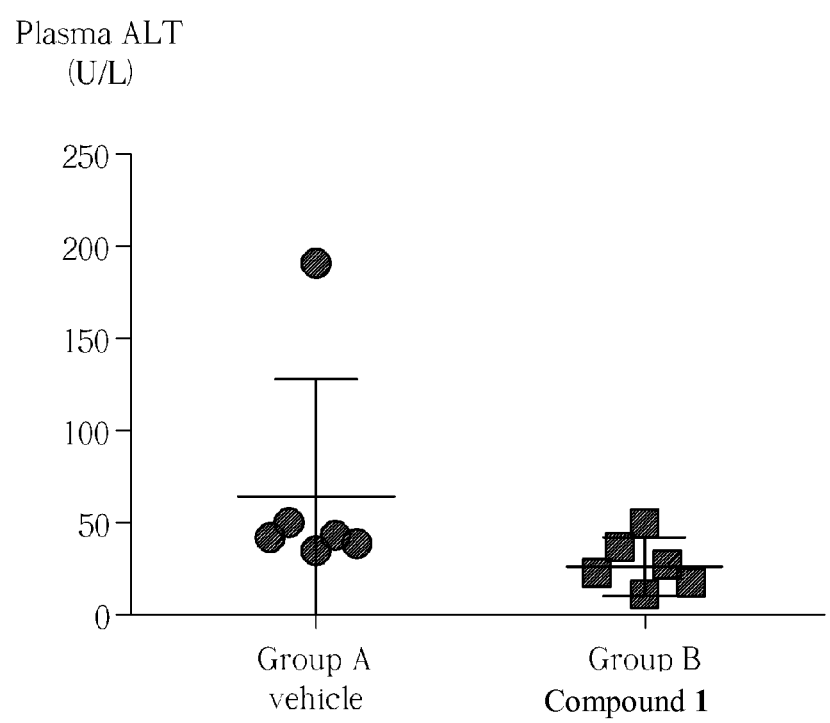

The aspartate aminotransferase (AST) and the alanine aminotransferase (ALT) are important enzymes in the amino acid synthesis for the human organs such as liver, heart, muscles, etc. AST and ALT are commonly measured clinically as a part of a diagnostic evaluation of hepatocellular injury, to determine liver health. These enzymes' content in serum is low under normal conditions. Significantly elevated levels of AST and ALT often suggest the existence of liver injury. FIG. 6 and FIG. 7 show diagrams of plasma AST and plasma ALT concentration (U/dL) for Group A and Group B, respectively. As shown in FIG. 6, Group B (the test compound, Compound 1) treatment seems to slightly reduce the plasma AST level compared to Group A (vehicle) treatment (Group A: 202±177 U/L, Group B: 141±35 U/L). As shown in FIG. 7, Group B (the test compound, Compound 1) treatment seems to slightly reduce the plasma ALT level compared to Group A (vehicle) treatment (Group A: 64±64 U/L, Group B: 34±10 U/L).

In summary, the test compound treatment decreased the plasma TG levels, tending to inhibit blood glucose levels, and slightly decreased the plasma AST and ALT. The test compound treatment also decreased the infiltration of inflammatory cells and fat deposition in the liver lobule. Moreover, the test compound tended to inhibit collagen deposition, shown in both Sirius red staining and collagen Type 3 staining, suggesting that the test compound has an anti-fibrotic effect on liver fibrosis steatohepatitis.

Fibrosis of Steatohepatitis Caused by Non-Chemical Injury

FIG. 8 to FIG. 14 show that the test compound, Compound 1 effectively decrease fibrosis of steatohepatitis liver cells induced by non-chemical injury. The decrease is assessed by evaluating the extent of liver injuries in liver fibrosis by histological analyses such as HE staining, Sirius red staining and collagen immunostaining, and further by plasma biochemical marker such as blood glucose, plasma alanine aminotransferase and plasma aspartate aminotransferase.

Figure 8:
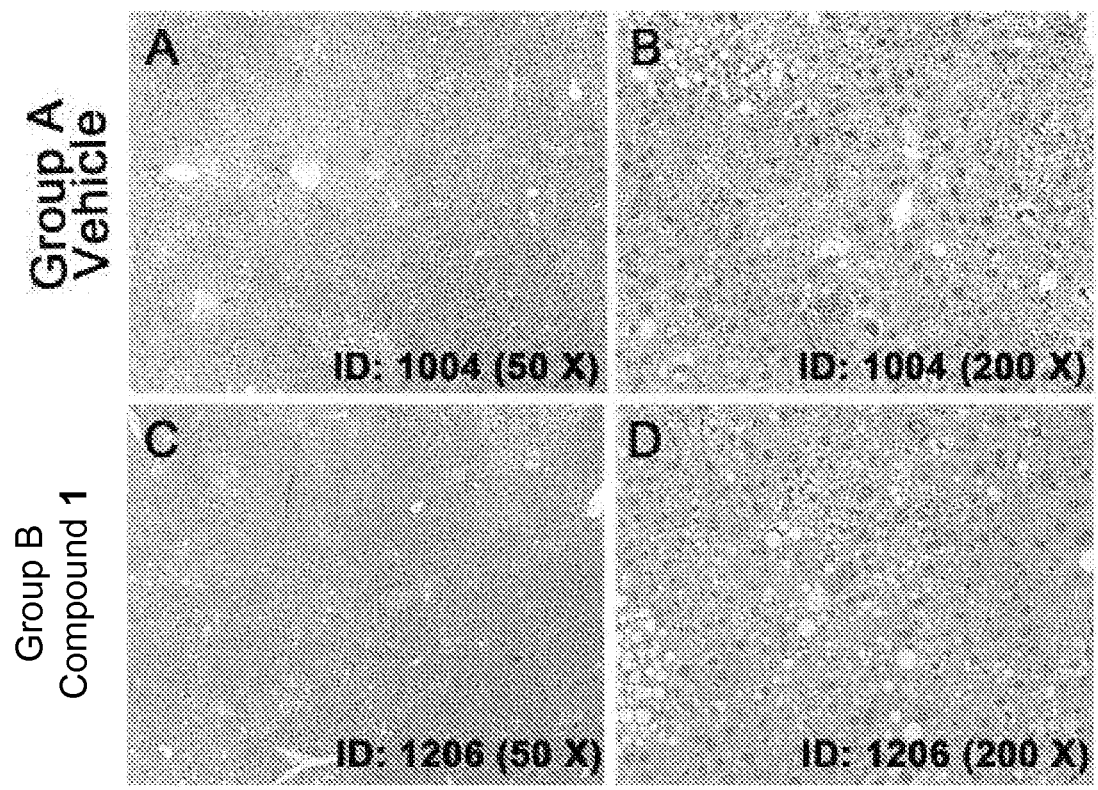
FIG. 8(A-D) shows representative photomicrographs of HE-stained sections of livers of Group A and Group B regarding fibrosis of steatohepatitis liver cells.

FIG. 8 shows the representative photomicrographs of HE-stained sections of livers of Group A and Group B, wherein FIGS. 8(A) and 8(C) show an enlargement ratio of 50×, and FIGS. 8(B) and 8(D) show an enlargement ratio of 200×. As shown in FIGS. 8(A) and 8(B), the Group A (vehicle) diagrams reveal infiltration of inflammatory cells, macro- and micro vesicular fat deposition, proliferated bile ducts, and hepatocellular ballooning in the liver sections. As shown in FIGS. 8(C) and 8(D), group B (the test compound, Compound 1) treatment tended to decrease the macrovesicular fat deposition compared to Group A.

Figure 9:
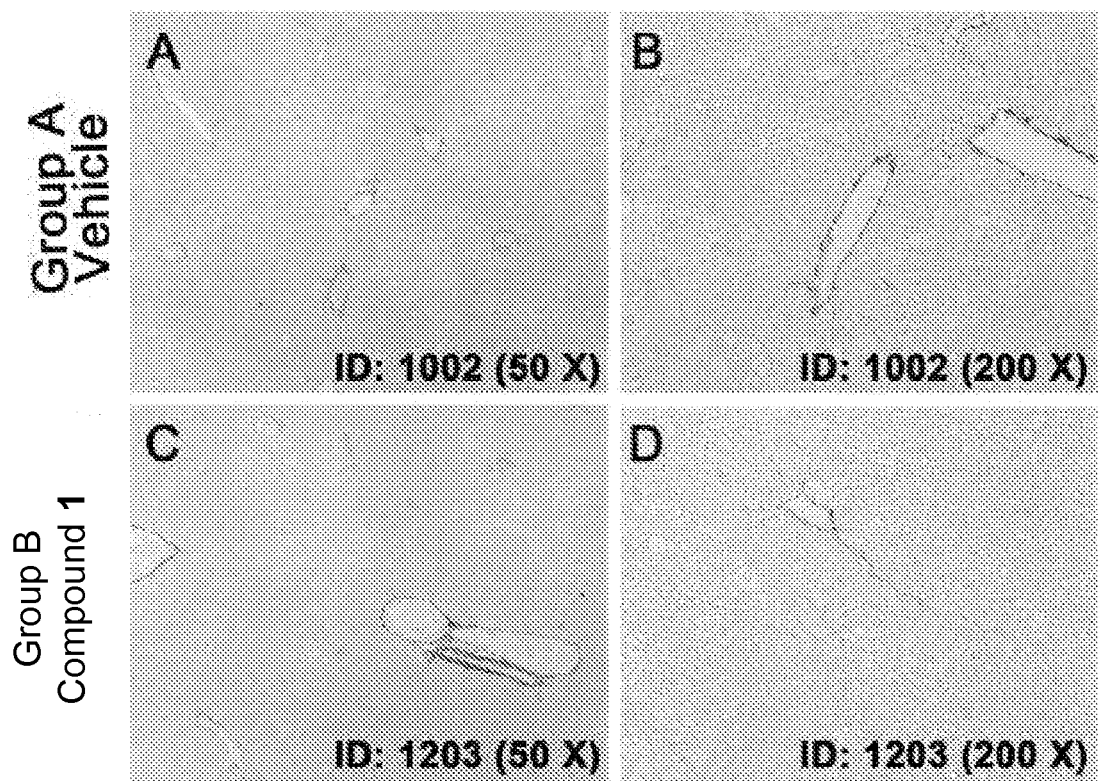
FIG. 9(A-D) shows representative photomicrographs of Sirius-red stained sections of livers of Group A and Group B regarding fibrosis of steatohepatitis liver cells.

FIG. 9 shows the representative photomicrographs of Sirius-red staining of livers of Group A and Group B, wherein FIGS. 9(A) and 9(C) show an enlargement ratio of 50×, and FIGS. 9(B) and 9(D) show an enlargement ratio of 200×. As shown in FIGS. 9(A) and 9(B), in Group A, Sirius red staining demonstrates collagen deposition around central veins, bile ducts and degenerative hepatocytes. In Group A treatment, central-to-central bridging fibrosis is observed, showing serious fibrosis in liver cells. As shown in FIGS. 9(C) and 9(D), in Group B (the test compound, Compound 1) treatment, the collagen deposition around the central veins and the bile ducts was reduced.

Figure 10:
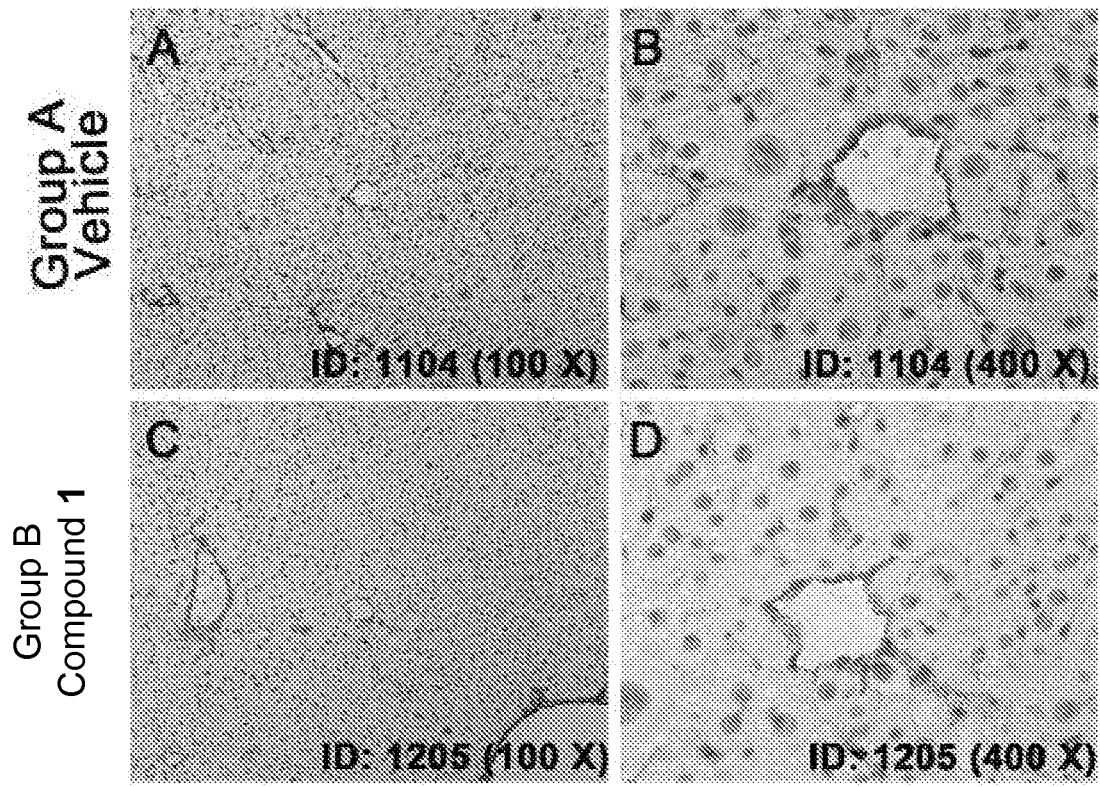
FIG. 10(A-D) shows representative photomicrographs of collagen Type 3-immunostained sections of livers of Group A and Group B regarding fibrosis of steatohepatitis liver cells.

FIG. 10 shows the representative photomicrographs of collagen Type 3-immunostained sections of livers of Group A and Group B, wherein FIGS. 10(A) and 10(C) show an enlargement ratio of 50×, and FIGS. 10(B) and 10(D) show an enlargement ratio of 400×. As shown in FIGS. 10(A) and 10(B), Collagen Type 3 staining shows accumulation of collagen fibers in the sinusoidal area, and around bile ducts and central veins in the Vehicle control Group A. As shown in FIGS. 10(C) and 10(D), the Group B (the test compound, Compound 1) treatment tended to reduce the thickness and/or the length of the collagen fibers in the sinusoidal area.

Figure 11:
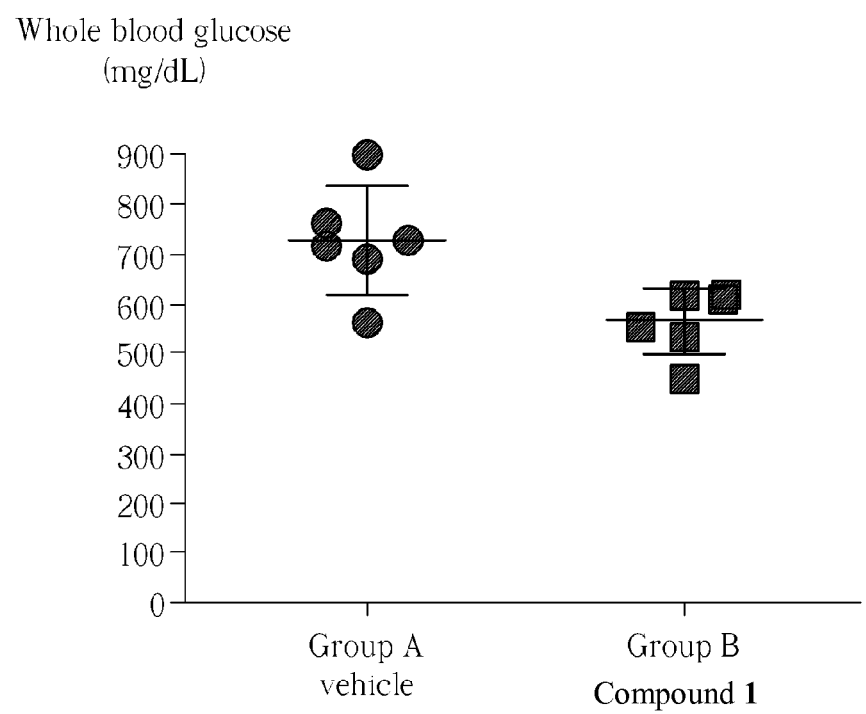
FIG. 11 shows diagrams of the whole blood glucose concentration (mg/dL) of Group A and Group B.

FIG. 11 shows the diagram of the whole blood glucose concentration (mg/dL) of Group A and Group B. As shown in FIG. 11, Group B treatment (the test compound, Compound 1) showed a significant decrease in the whole blood glucose level compared to the results of Group A treatment (Group A: 728±109 mg/dL, Group B: 566±65 mg/dL).

Figure 12:
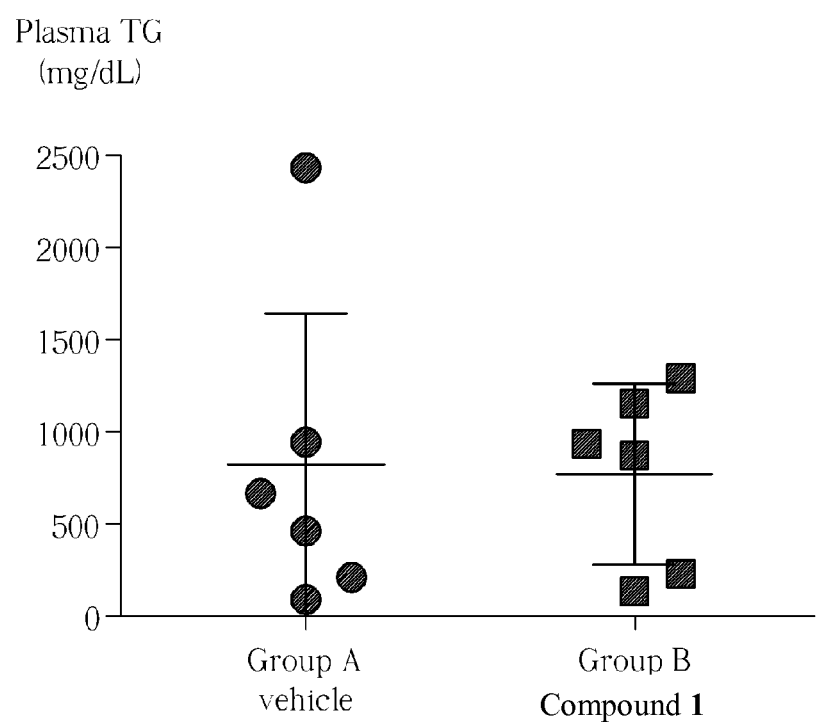
FIG. 12 shows diagrams of the plasma triglyceride concentration (mg/dL) of Group A and Group B.

FIG. 12 shows the diagram of the plasma triglyceride (TG) concentration (mg/dL) of Group A and Group B. As shown in FIG. 12, Group B treatment (the test compound, Compound 1) showed a slight decrease in the plasma TG compared to the results of Group A treatment (Group A: 758±877 mg/dL, Group B: 704±450 mg/dL).

Figure 13:
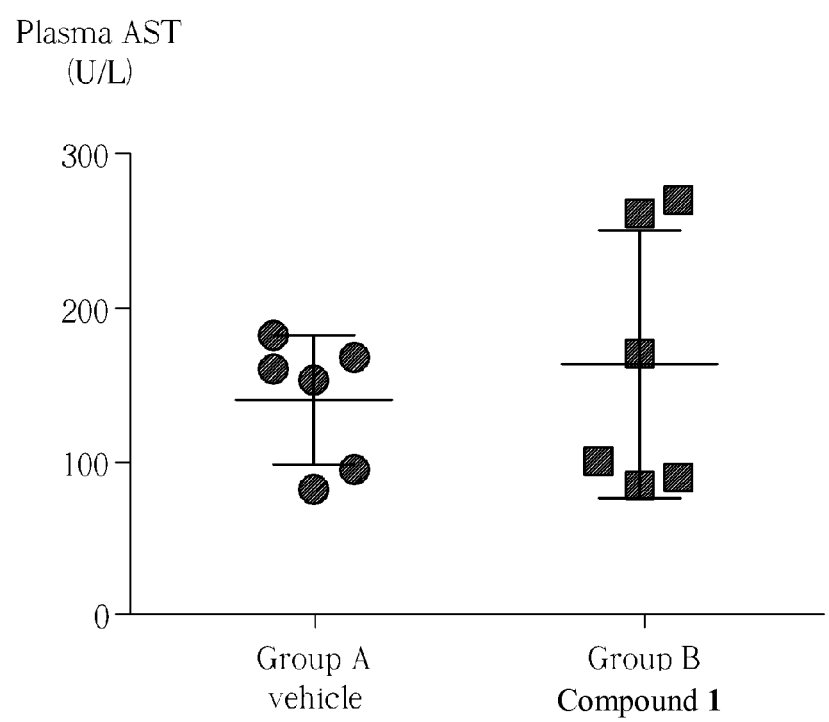
FIG. 13 and FIG. 14 respectively show diagrams of plasma AST and plasma ALT concentration (U/dL) of Group A and Group B.
Figure 14:
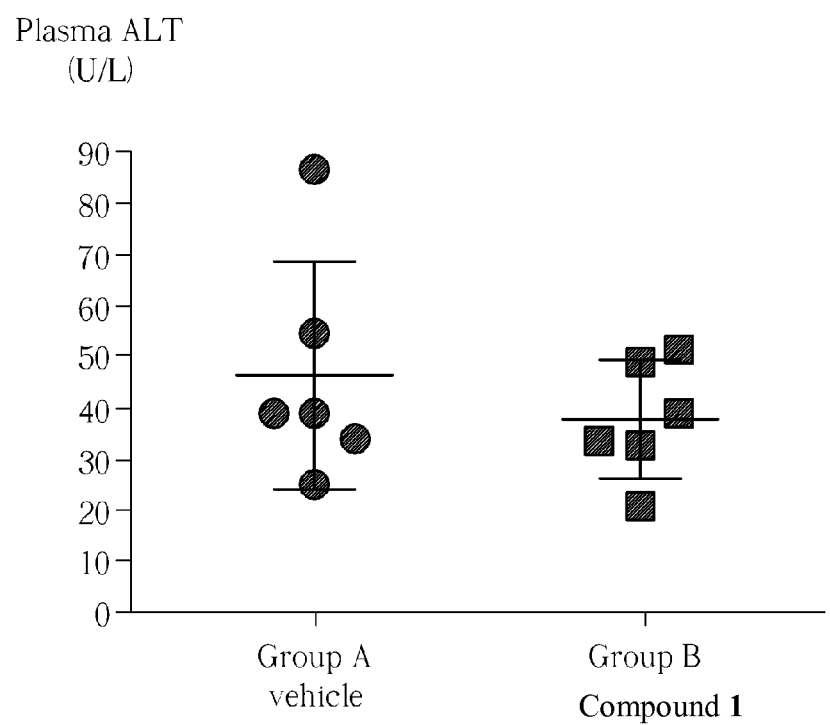

FIG. 13 and FIG. 14, respectively show diagrams of plasma AST and plasma ALT concentration (U/dL) for Group A and Group B. In FIG. 13, Group B (the test compound, Compound 1) treatment slightly increase the plasma AST level compared to Group A (vehicle) treatment, but the change is not significant (Group A: 143±42 U/L, Group B: 167±87 U/L). As shown in FIG. 14, Group B (the test compound, Compound 1) treatment reduces the plasma ALT level compared to Group A (vehicle) treatment (Group A: 47±22 U/L, Group B: 38±11 U/L).

In summary, the treatment with the test compound (e.g., Compound 1) decreased the blood glucose levels, the plasma TG levels, and tends to decrease the fat deposition in the liver lobule and the ALT levels, suggesting that the cyclohexenone compounds provided herein have an ameliorating effect on lipid and carbohydrate metabolism and a protective effect on liver injury caused by a high-fat diet. Also, the exemplary cyclohexenone compound (e.g., Compound 1) tended to inhibit collagen deposition, shown in both Sims red staining and collagen Type 3 staining, showing that the cyclohexenone compounds provided herein have an anti-fibrotic effect on liver steatohepatitis.

Taken together, the present invention successfully demonstrated that the test compound treatment effectively decrease the extents of fatty liver disease and liver fibrosis induced by metabolic syndrome, especially from high-fat diet treatment.

Example 3: Reduction of Fatty Liver Condition by the Composition Comprising Compound 1 and Ergosterol Except for the testing groups and treatment schedule, the materials and processes of Metabolic Syndrome" model, Histology analysis, Whole blood and plasma biochemistry and Fatty Liver Disease Caused by Non-Chemical Injury are similar to those stated in Example 2.

In control group (group A), six rats were fed with vehicle (corn oil from Sigma chemical co.) by means of stomach tubes. Six rats in group B were orally administered vehicle and the test compound (Compound 1) at a dose of 48 mg/kg twice a day (96 mg/kg per day) and ergosterol at a dose of 12 mg/kg twice a day (24 mg/kg per day). Six mice in group C were orally administered vehicle and the test compound (Compound 1) at a dose of 48 mg/kg twice a day (96 mg/kg per day).

Table 1 below shows the study timetable summary.

TABLE 1

The timetable of the study

| Time | Process |
| --- | --- |
| Day 0 | Birth |
| Day 2 | STZ treatment |
| Day 28 | Feeding high fat diet |
| Day 62 | Randomization |
| Day 63-Day 76 | Test substance administration |
| Day 77 | Sacrifice |

Table 2 shows the treatment schedule.

TABLE 2

Experimental groups with the substances they were fed with and their dosages

| Group | No. mice | Test substance | Dosage (mg/kg) | Volume (ml/kg) | Regiments |
| --- | --- | --- | --- | --- | --- |
| A | 6 | Vehicle control | — | 10 | Oral, twice a day, 9-11 weeks |
| B | 6 | The test compound | 48 | | |
| | | Ergosterol | 12 | | |
| C | 6 | The test compound | 48 | | |

HE Staining

FIG. 15 shows the representative photomicrographs of HE-stained sections of livers from Group A to Group C, wherein FIG. 15(A), 15(C), 15(E) show an enlargement ratio of 50× and FIG. 15(B), 15(D), 15(F) show an enlargement ratio of 200×. As shown in FIGS. 15(A) and 15(B), the Group A figures revealed infiltration of inflammatory cells, macro- and micro vesicular fat deposition, proliferated bile ducts and hepatocellular ballooning in the liver sections. As shown in FIGS. 15(C) and 15(D), treatment with combination of the test compound (Compound 1) and ergosterol decreased the macro vesicular fat deposition and the infiltration of inflammatory cells. The number of mitotic figures in hepatocytes is higher in group B compared to the group A. As shown in FIGS. 15(E) and 15(F), the treatment with the test compound alone tended to decrease the macro vesicular fat deposition but did not affect the infiltration of inflammatory cells.

From FIG. 15, it is recognized that the treatment with the test compound (Compound 1) and ergosterol (Group B) have the ability of reducing the macro vesicular fat deposition. Compared to the treatment with the test compound alone (Group C), the treatment with the test compound and ergosterol (Group B) further inhibit the inflammatory cells infiltration, thereby showing better anti-inflammatory effects with respect to Group C.

Sirius Red Staining

FIG. 16 shows the representative photomicrographs of Sirius-red stained of livers from Group A to Group C, wherein FIG. 16(A), 16(C), 16(E) show an enlargement ratio of 50× and FIG. 16(B), 16(D), 16(F) show an enlargement ratio of 200×. As shown in FIGS. 16(A) and 16(B), in group A, Sirius red staining show collagen deposition around central veins, bile ducts and degenerative hepatocytes, showing central-to-central bridging fibrosis and indicating serious fibrosis steatohepatitis. As shown in FIGS. 16(C) and 16(D), the treatment with the combination of the test compound (Compound 1) and ergosterol tended to decrease the collagen deposition. As shown in FIGS. 16(E) and 16(F), the cyclohexenone alone treatment tended only slightly to decrease the collagen deposition compared to that in the control group.

In summary, both the treatments with the cyclohexeone compound provided herein (e.g., Compound 1) and ergosterol treatment (Group B) and the treatment with the test compound alone (Group C) tend to inhibit collagen deposition, and thus prevent liver fibrosis. More specifically, the treatment with the combination of the cyclohexenone compound provided herein (e.g., Compound 1) and ergosterol provides a better anti-liver-fibrosis ability compared to the treatment with the test compound alone.

Immunohistochemistry of Collagen Type 3

FIG. 17 shows the representative photomicrographs of collagen Type 3-immunostained sections of livers from Group A to Group C, wherein FIG. 17(A), 17(C), 17(E) show an enlargement ratio of 100× and FIG. 17(B), 17(D), 17(F) show an enlargement ratio of 400×. As shown in FIGS. 17(A) and 17(B), Collagen Type 3 staining shows accumulation of collagen fibers in the sinusoidal area and around bile ducts and central veins in the Vehicle control group. As shown in FIGS. 17(C), 17(D), 17(E) and 17(F), the combination of cyclohexenone (e.g., Compound 1) and ergosterol treatment and the cyclohexenone alone treatment tended to reduce the collagen deposition proved by the decrease of the thickness of the collagen fibers in the sinusoidal area, indicating their anti-fibrosis ability.

Example 4: Study of Compound 1 in Patients with Diabetes and Presumed NAFLD

The primary objectives of this study are to assess, in patients with Type 2 diabetes mellitus (DM) and presumed nonalcoholic fatty liver disease (NAFLD), the following:
The safety and tolerability of multiple doses of Compound 1;
The effects of 2 dose levels (50 mg and 100 mg) of Compound 1 on insulin resistance and glucose homeostasis;
Effects of Compound 1 on hepatocellular function as measured by assessment of liver enzymes and biochemical markers of hepatic and metabolic function and inflammation.
Study Type: Interventional
Study Design: Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Insulin Resistance and Glucose Homeostasis [Time Frame: baseline and 6 weeks] [Designated as safety issue: No]
The primary objective of assessing changes in insulin resistance and glucose homeostasis will be attained by performing a euglycemic clamp procedure at baseline (Day 0) and at the end of 6 weeks of treatment (Day 43).

Secondary Outcome Measures:

Hepatocellular Function [Time Frame: baseline and 6 weeks] [Designated as safety issue: Yes]

Hepatocellular function as measured by assessment of liver enzymes and biochemical markers of hepatic and metabolic function

| Arms | Assigned Interventions |
|---|---|
| Active Comparator: 50 mg Compound 1 | Drug: Compound 1 50 mg by mouth once daily, 100 mg by mouth once daily |
| Active Comparator: 100 mg Compound 1 | Drug: Compound 1 100 mg by mouth once daily, 200 mg by mouth once daily |
| Placebo Comparator: Placebo | Drug: Placebo Placebo |

DETAILED DESCRIPTION

This is a multi-center, double-blind, randomized, placebo-controlled, multiple-dose, parallel-group study. Three (3) cohorts of 12 patients each will receive either placebo, 50 mg Compound 1, or 100 mg Compound 1 by mouth daily for 6 weeks.

The primary objective of assessing changes in insulin resistance and glucose homeostasis will be attained by performing a euglycemic clamp procedure at baseline (Day 0) and at the end of 6 weeks of treatment (Day 43). Other endpoints will be evaluated by monitoring adverse experiences; vital signs; clinical laboratory values; plasma drug and metabolite concentrations; and general health and well-being.

Eligibility

Ages Eligible for Study: 18 Years to 75 Years

Genders Eligible for Study: Both

Accepts Healthy Volunteers: No

Inclusion Criteria:

Type 2 diabetes, defined by the American Diabetes Association (ADA), as one of the following criteria:

Symptoms of diabetes plus casual plasma glucose concentration>200 mg/dL (11.1 mmol/L) or Fasting plasma glucose>126 mg/dL (7.0 mmol/L) or 2-hour post-load glucose>200 mg/dL (11.1 mmol/L) during a 75 g oral glucose tolerance test (GTT).

Presumed NAFLD, defined by one of the following criteria:

Alanine aminotransferase (ALT)≥47 U/L for females and ≥56 U/L for males

Aspartate aminotransferase (AST)≥47 U/L for females and ≥60 U/L for males

Enlarged liver (demonstrated by ultrasound or other imaging technique)

Diagnostic histological findings shown on prior biopsy (in the last 5 years).

Exclusion Criteria:

Bilirubin>2×ULN

ALT>155 U/L for females and >185 U/L for males.

AST>155 U/L for females and >200 U/L for males.

Patients taking any antidiabetic medications, with the exception of metformin and sulfonylureas. If the HbA1c is <11%, patients may be enrolled who have been withdrawn from all other diabetic medications as specified in the protocol, at the discretion of the Principal Investigator.

Example 5: Oral Formulation

To prepare a pharmaceutical composition for oral delivery, 100 mg of an exemplary Compound 1 is mixed with 100 mg of corn oil. The mixture is incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 6: Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 7: Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating non-alcoholic fatty liver disease (NAFLD) or non-alcoholic steatohepatitis (NASH) caused by non-chemical injury in a patient, comprising (a) selecting a patient having NAFLD or NASH caused by non-chemical injury, and (b) administering to said patient an effective amount of a compound

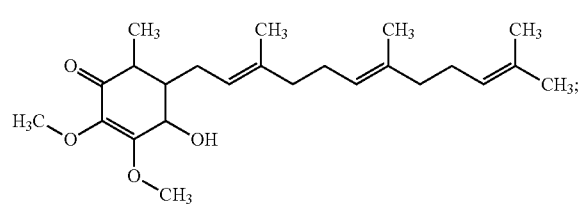 [SMILES: COC1=C(OC)C(O)C(C/C=C(\C)CC/C=C(\C)CCC=C(C)C)C(C)C1=O]

or a pharmaceutically acceptable salt, or solvate thereof in combination with ergosterol.

2. The method of claim 1, wherein the amounts of the compound in combination with ergosterol range from 50% (w/w) to 90% (w/w) and 50% (w/w) to 10% (w/w), respectively.

* * * * *